United States Patent [19]

Cappucci

[11] Patent Number: 5,098,389
[45] Date of Patent: Mar. 24, 1992

[54] HYPODERMIC NEEDLE ASSEMBLY

[75] Inventor: Patrick J. Cappucci, St. Paul, Minn.

[73] Assignee: Becton, Dickinson and Company, Franklin Lakes, N.J.

[21] Appl. No.: 546,148

[22] Filed: Jun. 28, 1990

[51] Int. Cl.[5] ............................................. A61M 5/00
[52] U.S. Cl. .................................. 604/158; 604/164; 604/170
[58] Field of Search ................ 604/158, 159, 170, 164

[56] References Cited

U.S. PATENT DOCUMENTS

| | | | |
|---|---|---|---|
| 3,477,423 | 11/1969 | Griffith . | |
| 3,792,703 | 2/1974 | Moorehead | 604/158 |
| 3,840,008 | 10/1974 | Noiles | 128/221 |
| 4,529,399 | 7/1985 | Groshong et al. | 604/170 |
| 4,627,841 | 12/1986 | Dorr | 604/158 |
| 4,828,548 | 5/1989 | Walter | 604/164 |
| 4,846,799 | 7/1989 | Tanaka et al. | 604/164 |
| 4,874,375 | 10/1989 | Ellison | 604/164 |
| 4,906,236 | 3/1990 | Alberts et al. | 604/164 |
| 4,940,458 | 7/1990 | Cohn | 604/158 |
| 4,994,040 | 2/1991 | Cameron et al. | 604/158 |
| 5,007,902 | 4/1991 | Witt | 604/170 |

OTHER PUBLICATIONS

Becton, Dickinson and Company Sales Brochure for Precision Cut TM Soft Tissue Biopsy Needle.

*Primary Examiner*—Paul J. Hirsch
*Attorney, Agent, or Firm*—John L. Voellmicke

[57] ABSTRACT

A hypodermic needle assembly is provided which may be used for retrobulbar injections. The assembly includes a substantially rigid handle, a short introducer needle mounted to the handle, a hollow, blunt-ended cannula mounted to the handle and slidable within the introducer needle, the cannula being mounted to the handle in such a manner that it cannot extend more than a selected distance beyond the end of the introducer needle. The cannula is mounted to a hub which is adapted for receiving a syringe. A plunger is mounted to the hub and includes an elongated body portion extending substantially parallel to the cannula. The plunger is engageable with two abutments formed within the housing for controlling the depth of insertion of the cannula within the body.

17 Claims, 7 Drawing Sheets

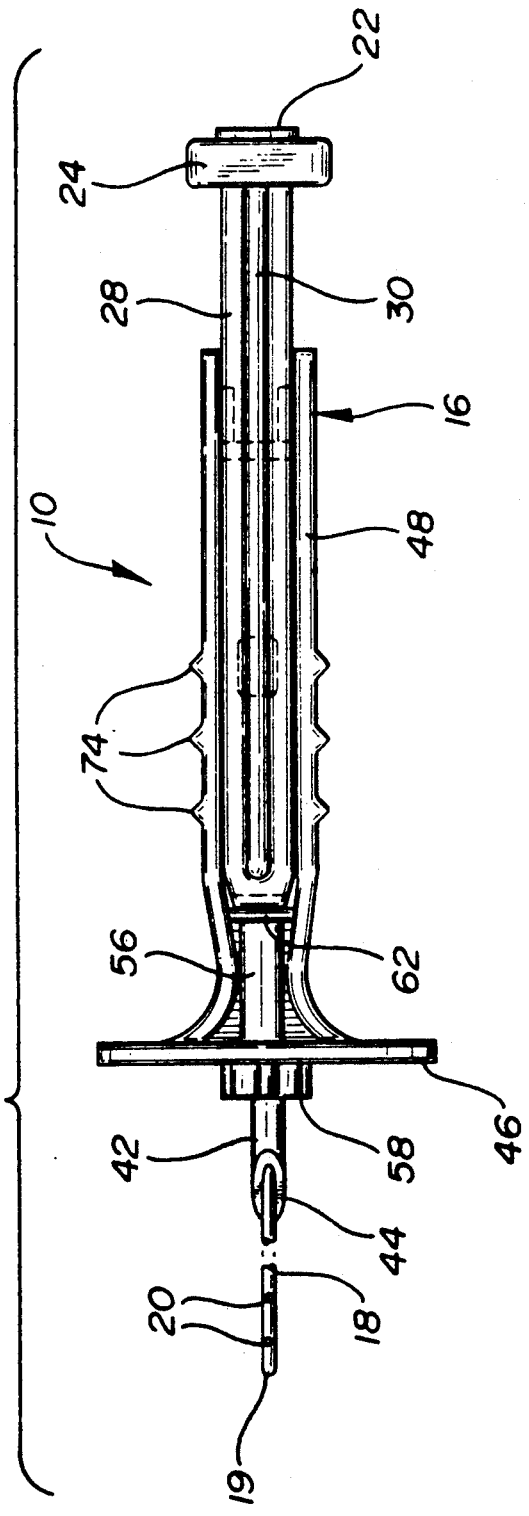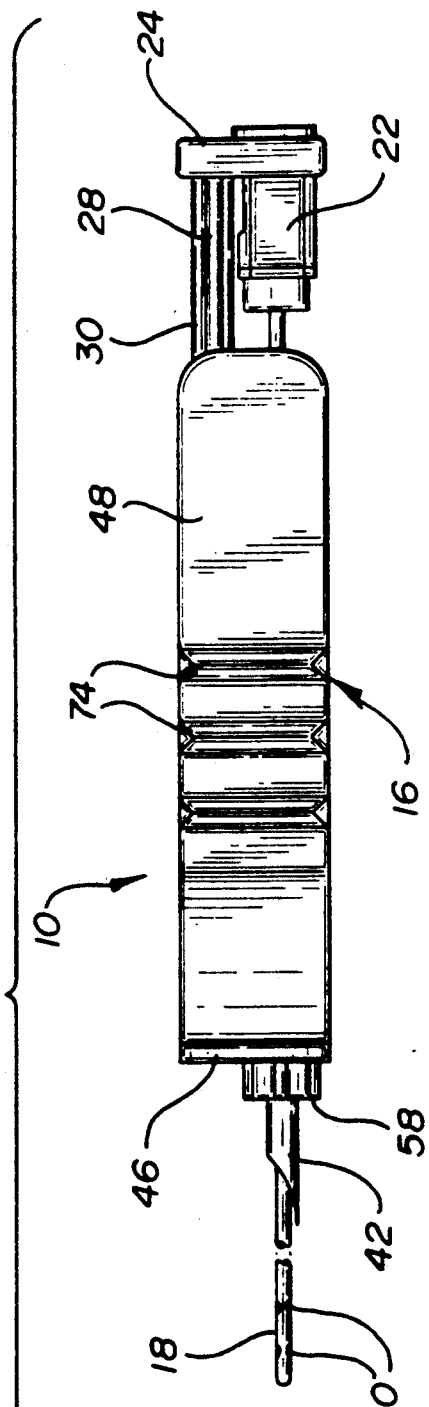

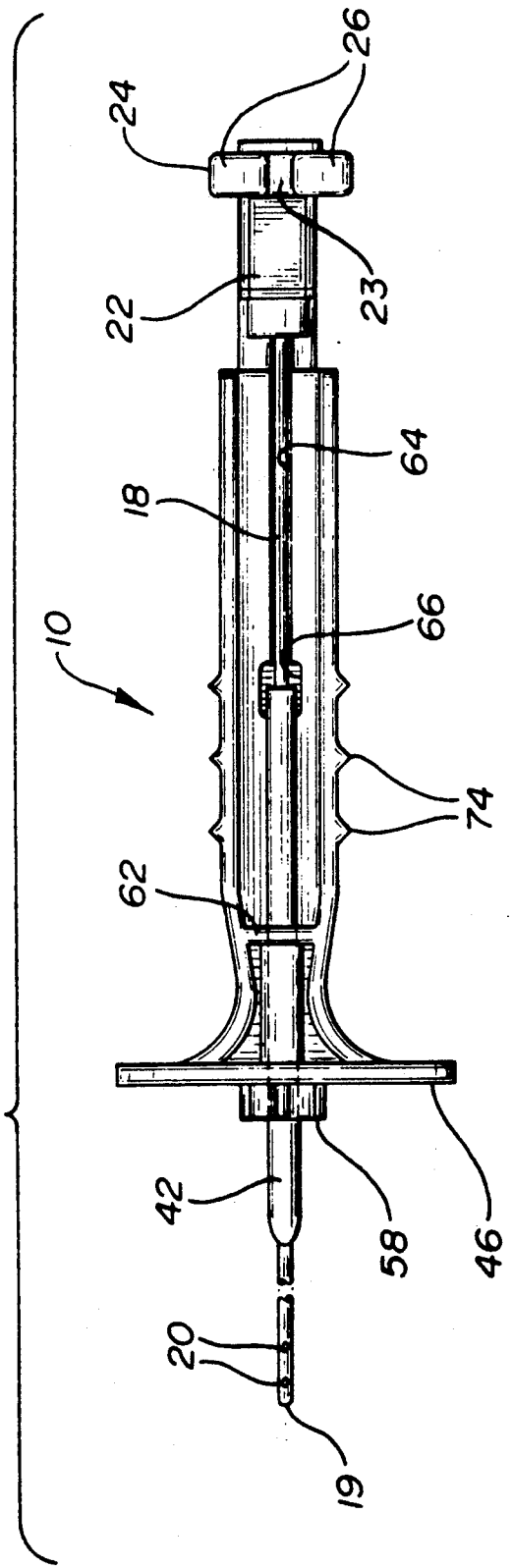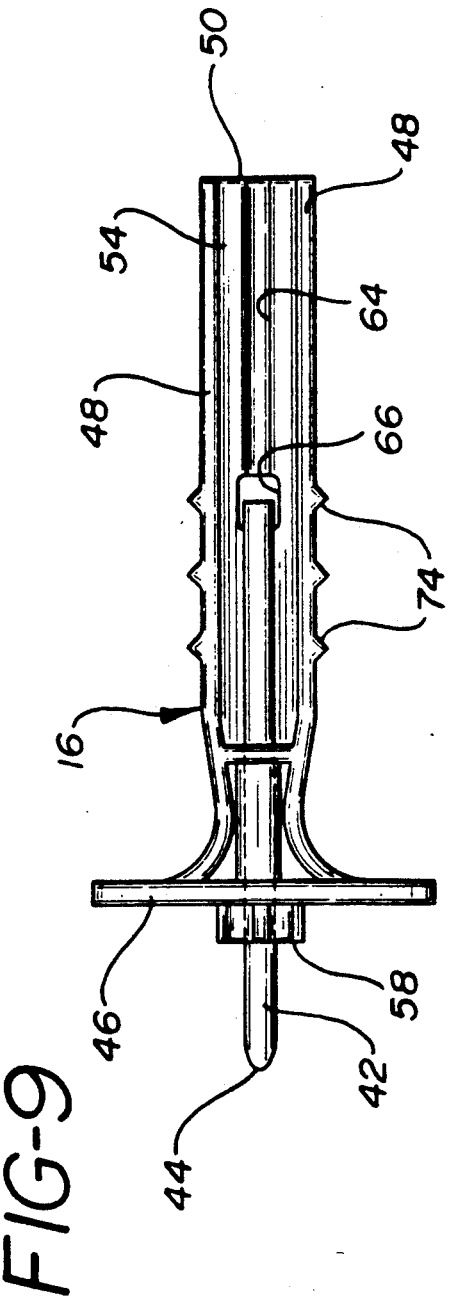

HYPODERMIC NEEDLE ASSEMBLY

BACKGROUND OF THE INVENTION

1. Field of the Invention

The field of the invention relates to hypodermic needle assemblies of the type including a pair of telescopically mounted cannulas.

2. Brief Description of the Prior Art

Hypodermic needle assemblies are employed for injecting various fluids within the body, such as medicaments, anesthetics and the like. Such assemblies require cannulas having sharp points in order to penetrate the skin and/or other tissue.

Needle assemblies have been developed which limit the depth of tissue penetration of sharp-pointed cannulas. Collars of enlarged diameter have often been used for this purpose. It is also known to provide a second, blunt-ended cannula telescopically mounted within a sharp-pointed cannula. The second cannula may be advanced beyond the end of the sharp-pointed cannula, and can be used to administer a hypodermic injection at a selected tissue depth. The blunt end thereof reduces the danger of damaging a nerve, a blood vessel of other tissue. U.S. Pat. No. 3,840,008 to Nailes discloses a hypodermic needle assembly of this type.

In the field of ophthalmic surgery, two options are generally available for anesthetization of the extrinsic muscles of the eye. These include retrobulbar and peribulbar injections using conventional, sharp-pointed needles. The retrobulbar technique involves injection of an anesthetic directly into the muscle cone. Akinesia is thereby achieved quickly and thoroughly. However, the introduction of a sharp needle behind the globe must be accomplished very carefully to avoid damaging the optic nerve, perforating the globe, for rupturing blood vessels. Some surgeons have employed dull needles to reduce the possibility of complications, but this makes penetration of the skin more difficult.

Peribulbar injections are administered around the globe rather than behind it. This virtually eliminates the possibility of the above-mentioned complications associated with retrobulbar injections. However, the technique requires a greater volume of anesthetic to be injected, and longer periods of time must be allowed pre-operatively for diffusion of the anesthetic into the muscle cone. Such diffusion must often be aided by external massage or by application of a device known as a Honan Balloon. In addition, the surgeon is not assured to complete akinesia through the use of this technique. Accordingly, there is a need for a device capable of administering retrobulbar injections without the inherent risks associated therewith.

SUMMARY OF THE INVENTION

It is an object of the invention to provide a hypodermic needle assembly capable of injecting a fluid into a patient.

It is another object of the invention to provide such an assembly which may be safely employed for anesthetizing the extrinsic muscles of the eye.

A still further object of the invention is to provide a hypodermic needle assembly which facilitates skin penetration to a controlled depth, and which provides safe entry into body tissue or space with a cannula to a controlled depth.

In accordance with these and other objects of the invention, a hypodermic needle assembly is provided which includes a substantially rigid handle having a proximal end and a distal end, an introducer needle at the distal end of the handle, the introducer needle including a sharp end projecting from the handle, a hollow blunt-ended cannula slidably engaged with the handle and at least partially slidable through the introducer needle and outside the sharp end thereof, and means for preventing the cannula from projecting more than a selected distance beyond the sharp end of the introducer needle. Such means preferably include a plunger which is connected to a cannula hub and engages a stop within the handle. The handle also preferably includes a second stop which is engaged by the plunger once the cannula has been withdrawn to a selected position.

In accordance with a second embodiment of the invention, a cannula and plunger assembly is provided. The assembly includes an elongated cannula having a blunt end, and at least one side port adjacent to said blunt end portion, a hub secured to one end of the cannula, and an elongated plunger secured to the hub and extending substantially parallel with respect to the cannula. The plunger preferably includes a projection extending towards the cannula.

BRIEF DESCRIPTION OF THE DRAWINGS

FIG. 6 is a top plan view thereof;

FIG. 7 is a side elevation view thereof;

FIG. 8 is a bottom plan view thereof;

FIG. 9 is a bottom plan view of a handle and introducer needle assembly according to the invention;

DETAILED DESCRIPTION OF THE INVENTION

A hypodermic needle assembly 10 for safely injecting fluid within the body is provided. The assembly 10 is particularly useful for performing retrobulbar injections, but may be used for other applications as well.

Figure 1:
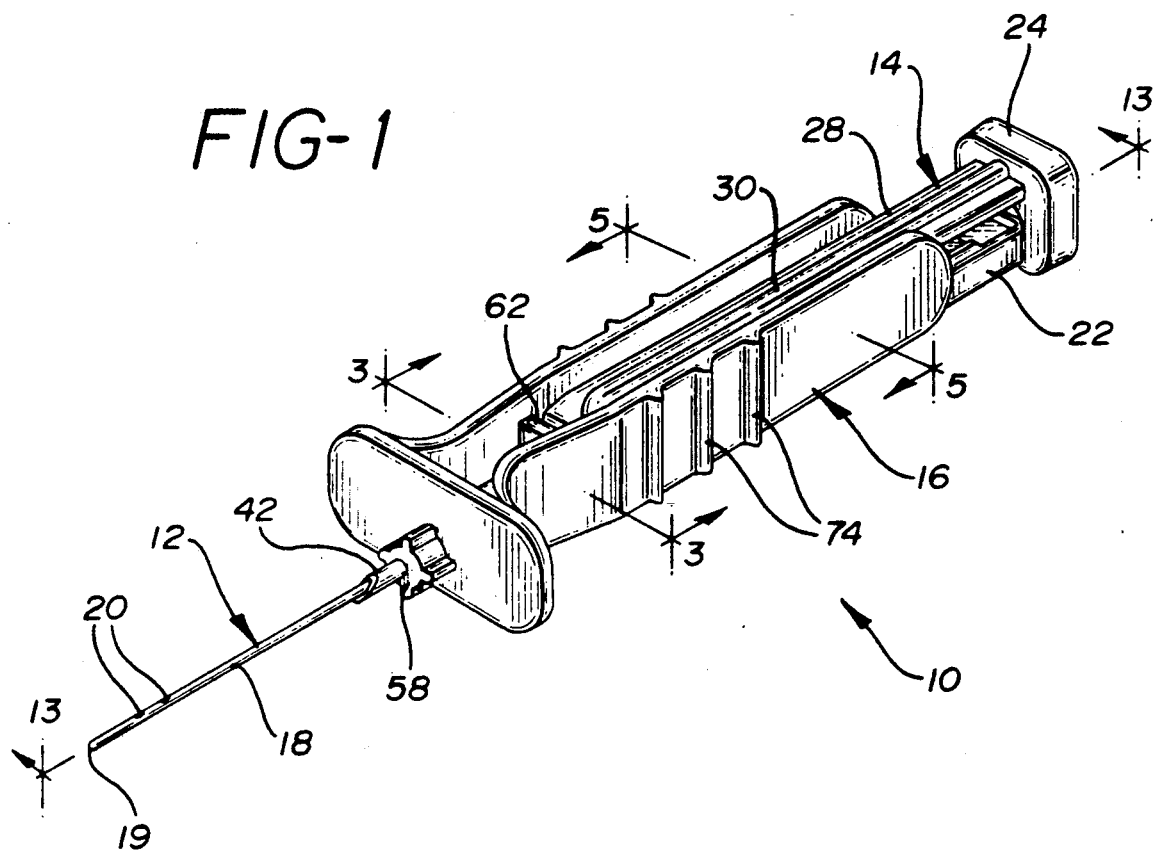
FIG. 1 is a top perspective view of a hypodermic needle assembly according to the invention.
Figure 2:
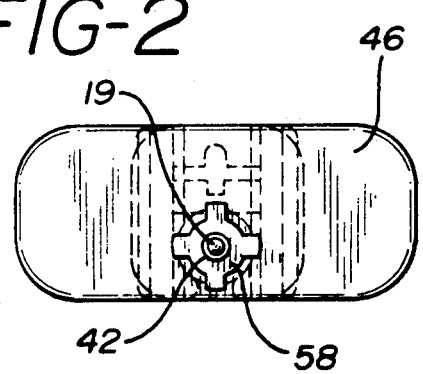
FIG. 2 is a front end view thereof.

Adverting to FIGS. 1-14, the assembly includes three major components: a cannula/hub assembly 12, a plunger 14, and a handle/introducer needle assembly 16. These structures are shown in assembled form in FIG. 1 and as exploded in FIG. 14. The cannula/hub assembly 12 includes a hollow, blunt, closed-ended cannula 18. A plurality of side ports 20, each of which may have a diameter of about 0.01 inch, provide access to the bore of the cannula 18. The front or distal end of the cannula 19 is preferably spherical to provide maximum safety. The rear end of the cannula 18 is secured to a hub 22. The hub includes a passage extending therethrough and is preferably transparent or translucent to allow the user to detect the presence of a fluid therein. The rear end of the hub is formed as a luer fitting to facilitate the attachment of a syringe thereto.

Figure 4:
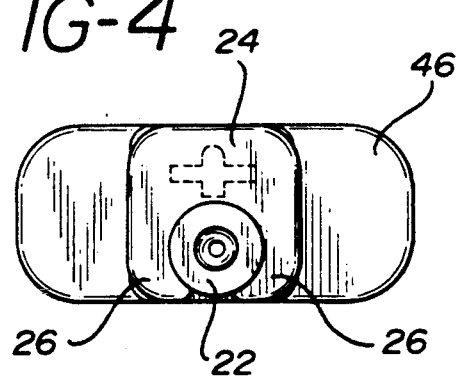
FIG. 4 is a rear end view thereof.
Figure 3:
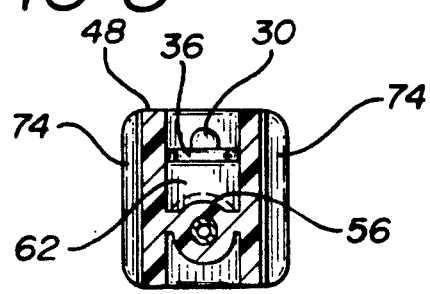
FIG. 3 is a cross-sectional view of the needle assembly of FIG. 1 taken along line 3—3 of FIG. 1.
Figure 5:
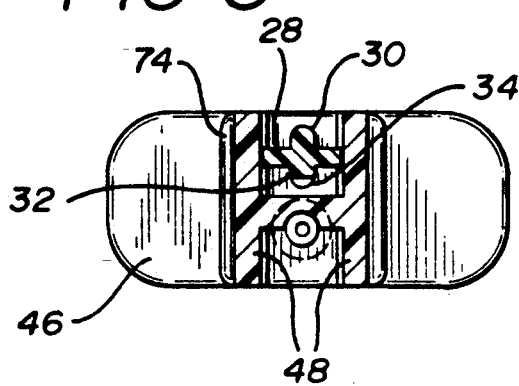
FIG. 5 is a cross-sectional view of the needle assembly of FIG. 1 taken along line 5—5 of FIG. 1.
Figure 10:
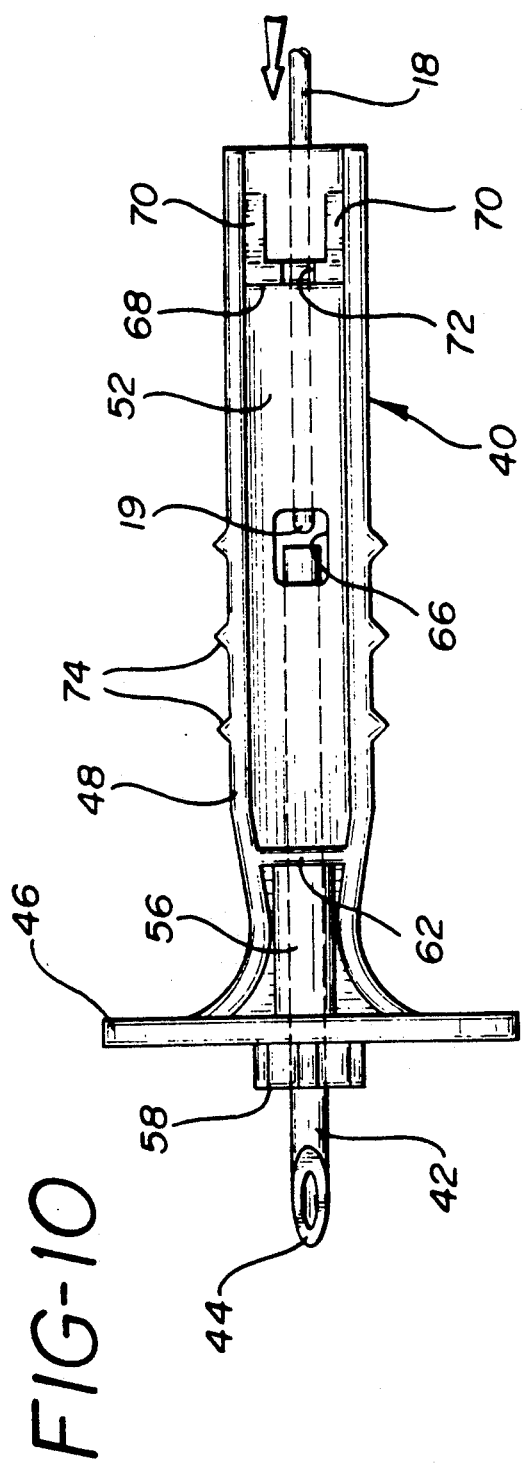
FIG. 10 is a top plan view showing the mounting of a cannula to the handle and introducer needle assembly.

The plunger 14, made of a plastic material, includes an enlarged rear end portion 24 including a pair of legs 26. Each of the legs 26 includes a generally sinusoidal inner surface. These inner surfaces define a cylindrical opening extending through the rear end portion. The plunger is mounted to the cannula/hub assembly 12 by urging the cylindrical end portion 23 of the hub 22 between the legs 26, thereby deflecting the legs outwardly until the hub snaps within the cylindrical opening as best illustrated in FIG. 4.

The plunger 14 includes an elongated body portion which extends substantially parallel to the cannula 18 when the rear end portion 24 of the plunger is secured to the hub 22. The body portion is comprised of a substantially flat, laterally extending wall 28 including integral, elongated, longitudinal ribs 30,32 extending above and below the flat wall, respectively, as shown in FIGS. 5 and 11-13. As shown most clearly in FIG. 11, a semicylindrical projection 34 is formed near the front end of the lower rib 32. The front end of the plunger 14 is defined by a downwardly extending wall 36. A notch 38 is defined between the rear end of the wall 36 and the front end of the projection 34.

The handle/introducer needle assembly 16 is preferably comprised of an integrally molded plastic handle 40 and a metal introducer needle 42 secured to the handle. Other materials may be employed in constructing these parts. The handle is substantially rigid, being made from a rigid or semi-rigid material. Such handles have been employed in prior art devices in conjunction with relatively long introducer needles as parts of a soft tissue biopsy device.

The introducer needle 42 includes an elongated cylindrical body having a longitudinal bore extending therethrough. The front end of the needle 42 includes a bevelled tip 44 which is sufficiently sharp to easily penetrate the skin. The rear end of the needle is substantially blunt. The introducer needle has an inner diameter which is slightly larger than the outside diameter of the cannula 18 so that the latter can easily slide therein. When the hypodermic needle assembly 10 is used for retrobulbar injections, the cannula may be formed from a twenty-six gauge tube, the outside diameter of which is about 0.018 inches.

The handle 40 includes a front flange 46 and an elongated body portion including a pair of opposing walls 48 extending rearwardly from the front flange. A third, horizontal wall 50 connects the two opposing walls 48 and also extends rearwardly with respect to the front flange. This third wall 50 includes a top surface 52 and a bottom surface 54, each of which is substantially planar. The top and bottom surfaces of the third wall 50 form substantially right angles with the respective inner surfaces of the two opposing walls 48.

Figure 13:
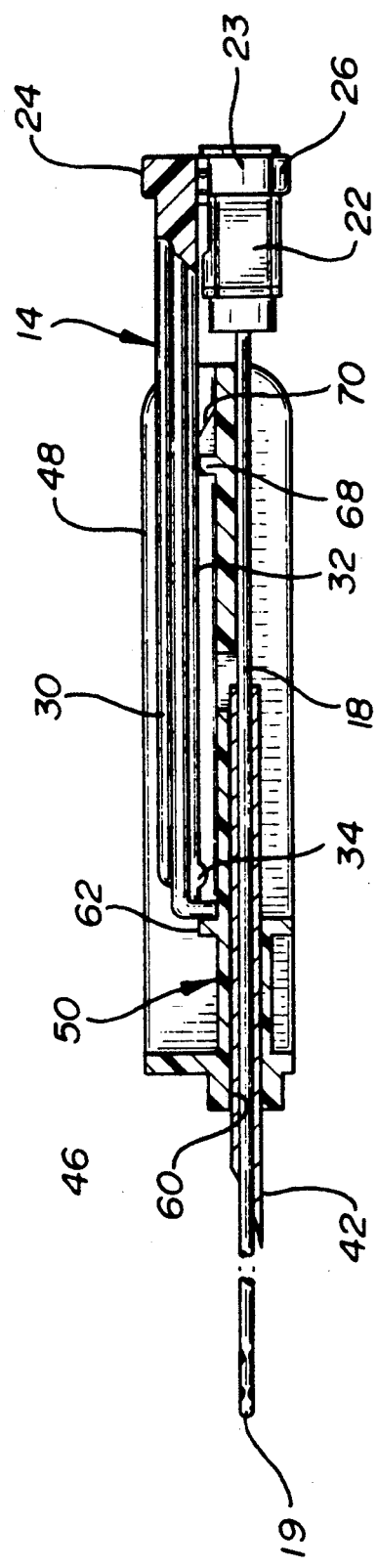
FIG. 13 is a cross-sectional side elevation view of the hypodermic needle assembly wherein the cannula is in the fully extended position with respect to the introducer needle.
Figure 14:
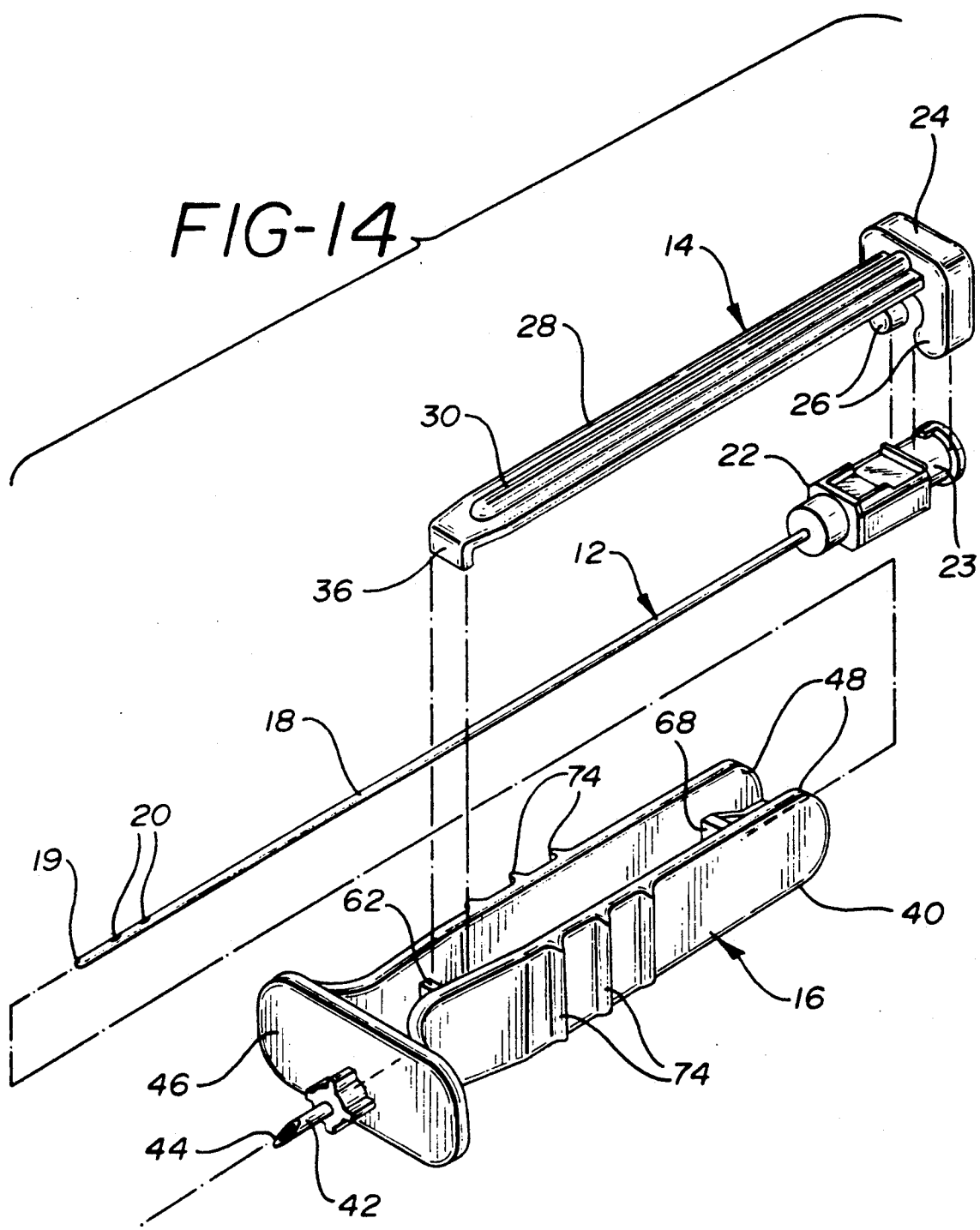
FIG. 14 is an exploded, top perspective view of the hypodermic needle assembly.

A cylindrical housing 56 is adjoined to and extends rearwardly from the rear surface of the front flange 46. A hub 58 adjoins the front surface of the flange 46 and projects a short distance therefrom. The hub 58 includes a substantially flat front surface. A longitudinal bore 60, as shown in FIG. 13, extends through the hub 58 and housing 56. The introducer needle 42 extends through this bore 60 and projects a short distance, e.g., about one to two centimeters, beyond the hub 58.

The rear end of the cylindrical housing 56 adjoins a lateral wall 62 which extends above and below the wall 50 connecting the two opposing walls 48 of the handle 40. This wall 62 is substantially perpendicular to the side and third walls 48, 50, which it adjoins, and is substantially parallel to the front flange 46. A semicylindrical, elongated groove 64, interrupted only by a rectangular opening 66 extending through the horizontal wall 50, extends from the vertical wall 62 to the rear end of the handle. This groove 64, as shown in FIG. 9, extends within the bottom surface 54 of the horizontally oriented wall 50. It is aligned with the bore 60 so that the rear end of the introducer needle 42 can be positioned therein. It also helps to maintain the cannula 18, and thereby the plunger 14, in the desired lateral position, as shown in FIG. 8.

Figure 11:
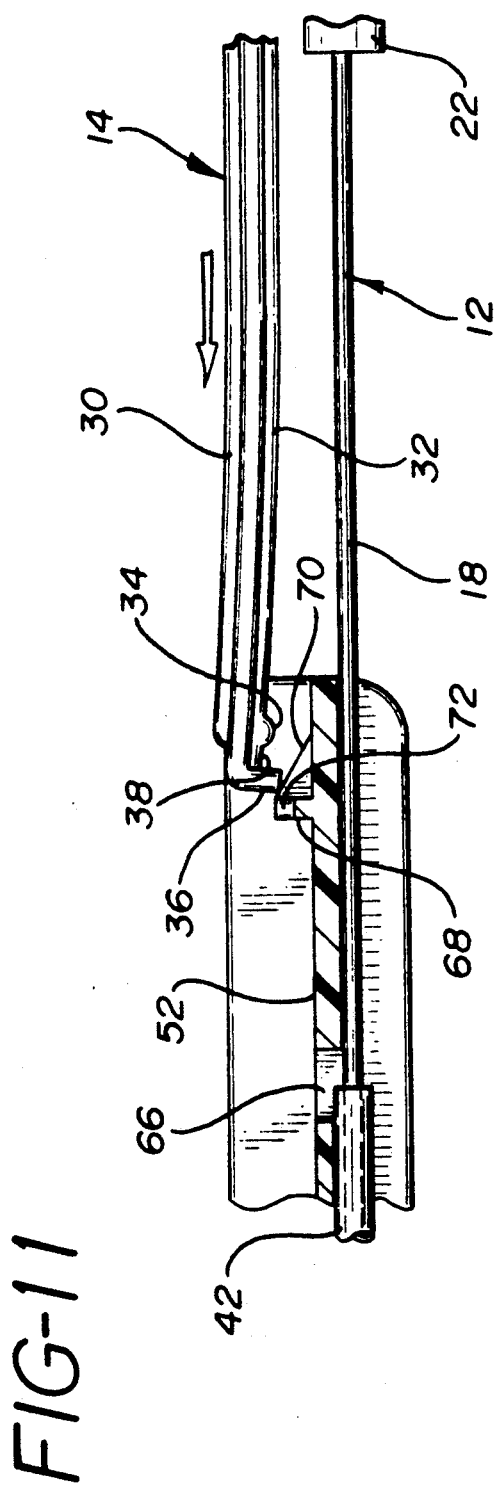
FIG. 11 is a cross-sectional side elevation view showing the assembly of a cannula/plunger assembly to the handle and introducer needle assembly.

A notched wall 68 extends upwardly from the top surface 52 of the horizontal wall 50 of the handle 40, as shown in FIGS. 10-13. This laterally extending wall 68 adjoins each side wall 48 of the handle. A pair of ramps 70 adjoin each end of the notched wall 68, and are preferably integral therewith. Each ramp includes a downwardly inclined surface which adjoins the top surface 52 of the horizontal wall 50 near the rear end of the handle 40. The distance between the inner edges of the ramps is less than the width of the downwardly extending wall 36 of the plunger 14, even though the front end of the plunger 14 is slightly tapered. This allows the bottom surface of the downwardly extending wall 36 to engage the upper surfaces of the ramps 70 when the plunger 14 is assembled to the handle 40, as shown in FIG. 11.

Figure 12:
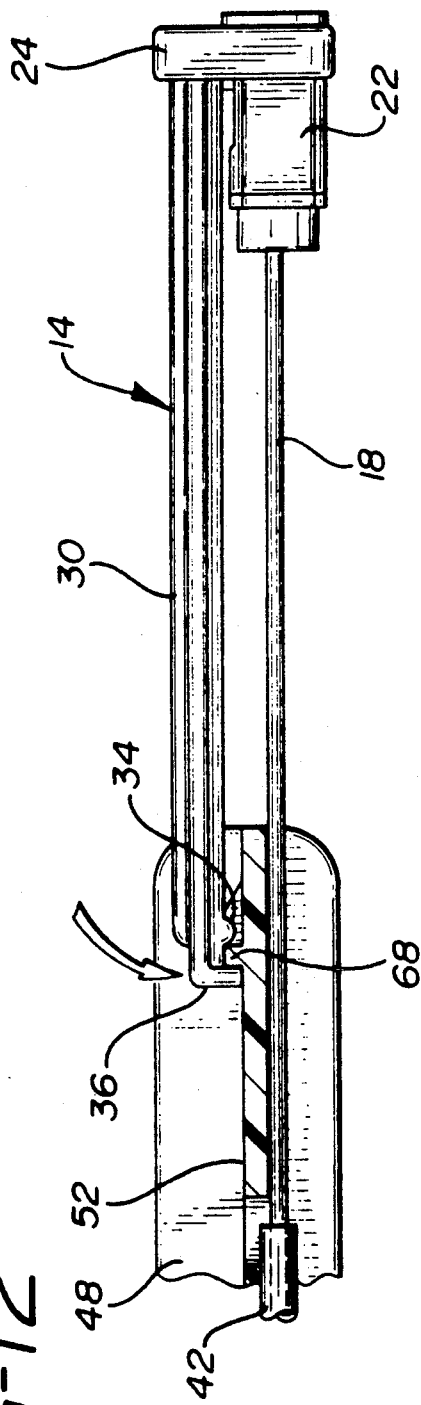
FIG. 12 is a cross-sectional side elevation view showing the cannula/plunger assembly locked in a withdrawn position with respect to the handle and introducer needle assembly.

The width of the notch 72 within the notched wall 68 is slightly larger than the widths of the lower rib 32 and projection 34 of the plunger 14. The depth of the notch 72 is the same as or slightly greater than the height of the lower rib 32, but less than the distance between the bottom surface of the lateral wall 28 of the plunger 14 and the lowest point of the projection 34. The plunger may accordingly be releasably engaged in a retracted position, as shown in FIG. 12, where the downwardly extending wall 36 is positioned on one side of the notched wall 68 and the projection 34 on the other side thereof. The projection 34 bears against the portion of the notched wall 68 beneath the notch 72 while in this position. Due to the semicylindrical configuration of the projection 34 and the flexibility of the plunger/cannula assembly, the projection will easily ride over the notched portion of the notched wall 68 when the plunger 14 is urged in the forward direction.

The overall configuration of the hypodermic needle assembly 10 is designed to facilitate its handling by a physician. The side walls 48 of the handle 40 each bow inwardly and then outwardly immediately before adjoining the front flange 46, thereby providing contours for thumb and middle finger support. Each of these walls also includes a plurality of parallel ribs 74.

The hypodermic needle assembly 10 is assembled by first affixing the cannula/hub assembly 12 to the plunger. This is accomplished by urging the cylindrical end portion of the hub 22 between the legs 26 of the enlarged end portion of the plunger 14 as described above. The resulting assembly is then oriented such that the cannula 18 is aligned with the groove 64 within the bottom surface 54 of the handle and the laterally oriented wall 28 of the plunger 14 is substantially parallel to the upper surface 52 of the handle. The cannula 18 is advanced through the groove 64 and into the bore of the introducer needle 42. The plunger 14 simultaneously follows the path shown in FIGS. 11-13, respectively. Once the front wall 36 of the plunger clears the notched wall 68, the plunger 14 and attached cannula 18 are permanently secured to the handle 40. The opposing walls 62, 68 extending upwardly from the upper surface 52 of the handle prevent the plunger 14 and attached cannula 18 from being displaced too far in either longitudinal direction. A protective sheath (now shown) may be mounted to the hub 58 in order to protect against accidental injury from the bevelled end 44 of the introducer needle 42.

The hypodermic needle assembly 10 described above can be used for injecting a fluid into selected areas of the body with greatly reduced risks of puncturing blood vessels or other tissue with the sharp end of a needle. When employed for administering retrobulbar injections, a syringe 76 (FIG. 15) is prefilled with a prescribed anesthetic and secured to the luer-type fitting defined by the hub 22. The plunger 14 is pulled back to its fully retracted position (FIG. 12) where it is locked in place by virtue of the notched wall 68 being engaged within the notch 38 of the plunger. The handle 40 is grasped with one hand while the other hand is used to located the orbital rim. The skin is then punctured with the bevelled end 44 of the introducer needle 42 at the junction of the lateral and middle thirds of the inferior orbital rim. The depth of insertion of the tip of the introducer needle is controlled by the front surface of the hub 58 which bottoms out on the orbital rim of the maxilla.

The handle 40 is held in place with one hand upon insertion of the introducer needle 42 into the body. The other hand is used to advance the inner, closed-ended cannula 18 through the introducer needle into the retrobulbar space. The cannula 18 is advanced until the front wall 36 of the plunger 14 engages the front, laterally extending wall 62 of the handle 40.

The distance between the front and rear lateral walls 62, 68 of the handle controls the depth of insertion of the cannula 18. When the plunger is in the fully retracted position, the forward end of the cannula adjoins the bevelled tip 44 of the introducer needle 42 without protruding therethrough. The distance between the above-described lateral walls 62, 68 will accordingly be substantially the same as the maximum distance that the cannula 18 can protrude from the introducer needle. The distance between these walls may be about one and one half inches for most retrobulbar injections.

Figure 15:
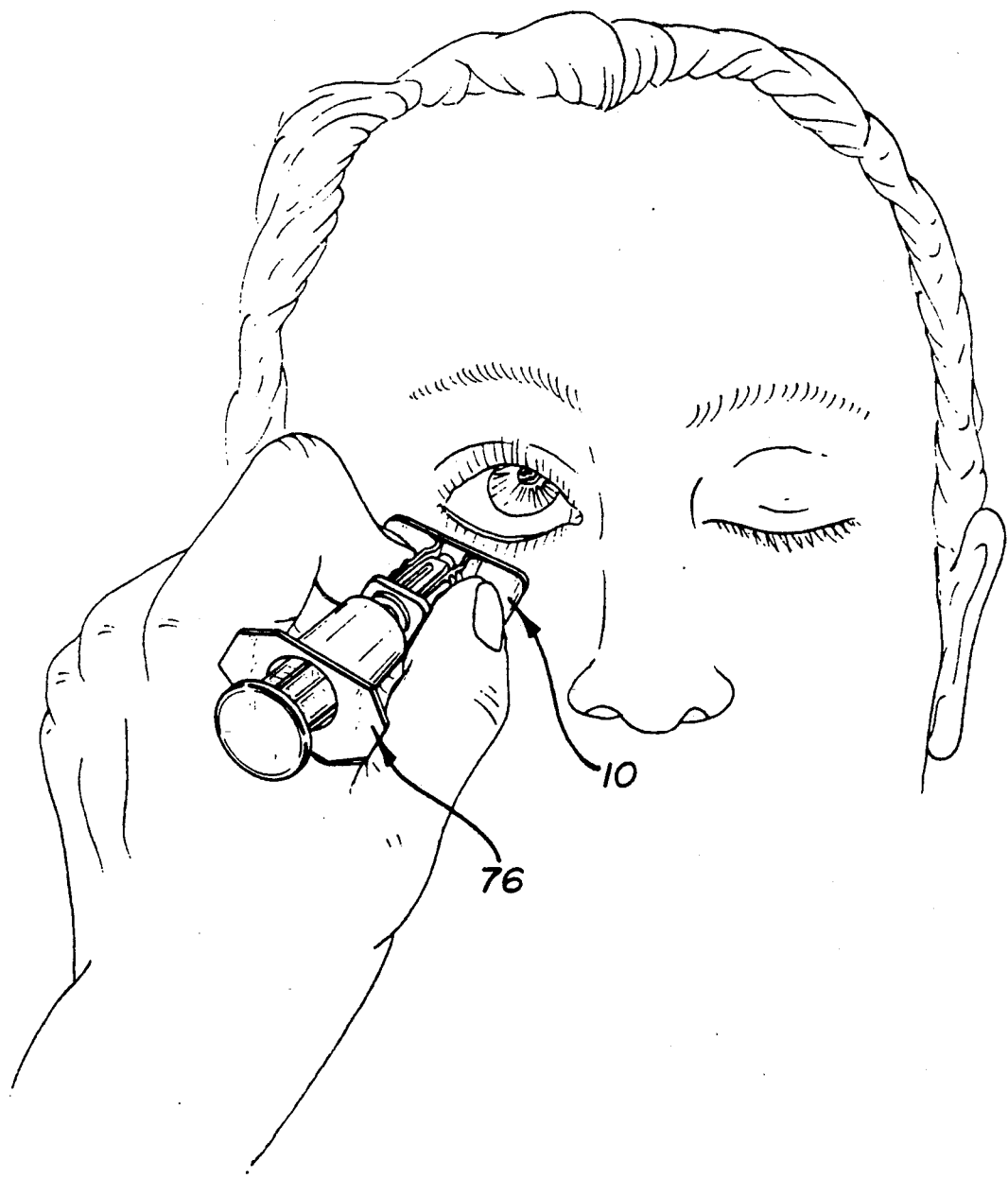
FIG. 15 illustrates the use of the hypodermic needle assembly being used to administer a retrobulbar injection.

The anesthetic is injected through the side ports 20 of the cannula 18 with the cannula in the fully extended position. Following injection, the cannula 18 is retracted and the assembly 10 is removed. Placement of the assembly 10 and the attached syringe 76 during the injection procedure is shown in FIG. 15.

By employing the assembly 10 in the above-described manner, the sharp, bevelled end of the introducer needle cannot come into contact with the globe, optic nerve or vessels behind the eye. This is due to the fact that the end of the introducer needle extends only about one half inch beyond the front surface of the hub 58. The depth of insertion of the cannula is also precisely controlled by the relative positions of the opposing lateral walls 62, 68 of the handle.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A hypodermic needle assembly comprising:
   a substantially rigid handle having a proximal end and a distal end;
   an introducer needle at said distal end of said handle, said introducer needle including a sharp end projecting from said handle;
   a rigid hollow cannula slidably engaged within said introducer needle, said cannula including a blunt end and at least one side port adjacent to said blunt end, said cannula being rigid enough to retain its shape while being used to administer a retrobulbar injection to the human eye;
   means for preventing said cannula from projecting more than a selected distance beyond said sharp end of said introducer needle; and
   means for withdrawing said cannula such that the blunt end thereof is entirely within said introducer needle.

2. An assembly as described in claim 1 wherein said handle includes a flange at said distal end, said sharp end of said introducer needle projecting distally from said flange.

3. An assembly as described in claim 2 wherein said handle includes an elongated body portion extending proximally from said flange, said body portion being contoured adjacent to said flange to facilitate gripping said handle with one or more digits.

4. An assembly as described in claim 3 including a hub secured to said cannula, a plunger secured to said hub, said plunger including an elongated body portion extending substantially parallel to said cannula.

5. An assembly as described in claim 4 wherein said plunger includes means for engaging said handle at two different positions upon said handle corresponding to two different longitudinal positions of said cannula with respect to said handle.

6. An assembly as described in claim 1 including a hub secured to said cannula, a plunger secured to said hub, said plunger including an elongated body portion extending substantially parallel to said cannula.

7. An assembly as described in claim 6 wherein said plunger includes means for engaging said handle at two different positions upon said handle corresponding to two different longitudinal positions of said cannula with respect to said handle.

8. An assembly as described in claim 7 including means for releasably engaging said plunger at one of said two different positions.

9. An assembly as described in claim 1 wherein said introducer needle projects between one and two centimeters beyond said handle.

10. An assembly as described in claim 6 wherein said plunger is detachably secured to said hub.

11. An assembly as described in claim 10 wherein said plunger includes an elongated rib extending towards said cannula, said handle including an elongated body portion including a notch, said rib being positioned within said notch.

12. A hypodermic needle assembly comprising:
a substantially rigid handle having a proximal end and a distal end, said handle including an elongated body portion having an upper surface and first and second abutment means extending from said upper surface;
an introducer needle at said distal end of said handle, said introducer needle including a sharp end projecting from said handle;
a hollow cannula slidably engaged within said introducer needle, said cannula including a blunt end and at least one side port adjacent to said blunt end;
a hub secured to said cannula, a plunger secured to said hub, said plunger including an elongated body portion extending substantially parallel to said cannula, said plunger including a projection extending towards said upper surface and engageable with said first and second abutment means, whereby said cannula extends outside said introducer needle when said projection engages said first abutment means but not when said projection engages said second abutment means;
means for preventing said cannula from projecting more than a selected distance beyond said sharp end of said introducer needle; and
means for withdrawing said cannula such that the blunt end thereof is entirely within said introducer needle.

13. An assembly as described in claim 12 including means for releasably retaining said plunger to said handle when said projection engages said second abutment means.

14. An assembly as described in claim 12 wherein said elongated body portion of said handle includes first and second opposing walls, a third wall extending laterally between said first and second opposing walls, said third wall defining said upper surface of said elongated body portion of said plunger extending above and substantially parallel to said upper surface.

15. An assembly as described in claim 14 wherein said first and second abutment means are first and second walls extending between said first and second opposing walls.

16. An assembly as described in claim 14 wherein said handle includes a flange, said first and second opposing walls adjoining said flange.

17. An assembly as described in claim 14 wherein said first and second opposing walls are bowed inwardly towards each other adjacent said flange to facilitate gripping said handle with one or more digits.

* * * * *